(12) United States Patent
Hunter et al.

(10) Patent No.: US 12,005,098 B2
(45) Date of Patent: Jun. 11, 2024

(54) ENZYME-RICH MALT EXTRACT (ERME) FORMULATIONS

(71) Applicant: PEPSIS LIMITED, Ledbury (GB)

(72) Inventors: John Hunter, Ledbury (GB); Rosemary Waring, Ledbury (GB)

(73) Assignee: PEPSIS LIMITED, London (GB)

( * ) Notice: Subject to any disclaimer, the term of this patent is extended or adjusted under 35 U.S.C. 154(b) by 350 days.

(21) Appl. No.: 16/461,977

(22) PCT Filed: Nov. 23, 2017

(86) PCT No.: PCT/GB2017/053516
§ 371 (c)(1),
(2) Date: May 17, 2019

(87) PCT Pub. No.: WO2018/096334
PCT Pub. Date: May 31, 2018

(65) Prior Publication Data
US 2019/0307859 A1 Oct. 10, 2019

(30) Foreign Application Priority Data
Nov. 23, 2016 (GB) ..................................... 1619789

(51) Int. Cl.
| | | |
|---|---|---|
| C12Q 1/40 | (2006.01) | |
| A23K 10/30 | (2016.01) | |
| A23K 10/38 | (2016.01) | |
| A23K 20/158 | (2016.01) | |
| A23K 20/189 | (2016.01) | |
| A23K 20/20 | (2016.01) | |
| A23K 20/24 | (2016.01) | |
| A23K 50/20 | (2016.01) | |
| A61K 9/14 | (2006.01) | |
| A61K 31/122 | (2006.01) | |
| A61K 31/19 | (2006.01) | |
| A61K 31/198 | (2006.01) | |
| A61K 31/20 | (2006.01) | |
| A61K 31/351 | (2006.01) | |
| A61K 31/352 | (2006.01) | |
| A61K 31/366 | (2006.01) | |
| A61K 31/7008 | (2006.01) | |
| A61K 33/06 | (2006.01) | |
| A61K 33/24 | (2019.01) | |
| A61K 36/185 | (2006.01) | |
| A61K 36/45 | (2006.01) | |
| A61K 36/889 | (2006.01) | |
| A61K 38/47 | (2006.01) | |
| A61K 45/06 | (2006.01) | |
| C12Q 1/34 | (2006.01) | |

(52) U.S. Cl.
CPC .............. *A61K 38/47* (2013.01); *A23K 10/30* (2016.05); *A23K 10/38* (2016.05); *A23K 20/158* (2016.05); *A23K 20/189* (2016.05); *A23K 20/24* (2016.05); *A23K 20/30* (2016.05); *A23K 50/20* (2016.05); *A61K 9/14* (2013.01); *A61K 31/122* (2013.01); *A61K 31/19* (2013.01); *A61K 31/198* (2013.01); *A61K 31/20* (2013.01); *A61K 31/351* (2013.01); *A61K 31/352* (2013.01); *A61K 31/366* (2013.01); *A61K 31/7008* (2013.01); *A61K 33/06* (2013.01); *A61K 33/24* (2013.01); *A61K 36/185* (2013.01); *A61K 36/45* (2013.01); *A61K 36/889* (2013.01); *A61K 45/06* (2013.01); *C12Q 1/34* (2013.01); *C12Q 1/40* (2013.01); *C12Y 302/01001* (2013.01); *C12Y 302/01002* (2013.01); *C12Y 302/0108* (2013.01); *A23V 2250/00* (2013.01); *A23V 2250/1578* (2013.01); *A23V 2250/1586* (2013.01); *A23V 2250/1612* (2013.01); *A23V 2250/1878* (2013.01); *A23V 2250/21* (2013.01); *Y02P 60/87* (2015.11)

(58) Field of Classification Search
CPC .... A23K 20/158; A23K 20/189; A23K 50/20; A23K 10/30; A23K 20/24; A61K 36/45; A61K 33/06; A61K 38/47; C12Q 1/40; C12Q 1/34; C12Y 302/01001; C12Y 302/01002; C12Y 302/0108; A23V 2250/1578; A23V 2250/21; A23V 2250/00; A23V 2250/1878
See application file for complete search history.

(56) References Cited

U.S. PATENT DOCUMENTS

| | | | |
|---|---|---|---|
| 3,713,840 A | 1/1973 | Quittenton | |
| 2009/0232949 A1 | 9/2009 | Stark | |
| 2016/0213029 A1 | 7/2016 | Bruggeman | |

FOREIGN PATENT DOCUMENTS

| | | | |
|---|---|---|---|
| CN | 105146188 A | 12/2015 | |
| EP | 1059041 A1 | 12/2000 | |
| GB | 2120787 A | 12/1983 | |

(Continued)

OTHER PUBLICATIONS

Cort WM. Antioxidant Properties of Ascorbic Acid in Foods. Advances in Chemistry. 1982;200:533-550.*

(Continued)

*Primary Examiner* — Lynn Y Fan
(74) *Attorney, Agent, or Firm* — Maine Cernota & Curran

(57) ABSTRACT

The present invention relates to compositions comprising: malt extract including a plurality of enzymatically active enzymes including at least fructanase and amylase; one or more medium-chain triglycerides (MCTs) and/or at least one biologically acceptable metal component and use of those compositions as veterinary and human medicaments.

16 Claims, No Drawings

(56) References Cited

FOREIGN PATENT DOCUMENTS

| WO | WO2008/002987 A2 | 1/2008 |
| WO | WO2013/136069 A2 | 9/2013 |
| WO | WO2016/007026 A1 | 1/2016 |

OTHER PUBLICATIONS

Mehta et al. Bacterial and Archaeal a-Amylases: Diversity and Amelioration of the Desirable Characteristics for Industrial Applications. Front. Microbiol. 2016;7(1129):1-21.*

Shahidi et al. Phenolics and polyphenolics in foods, beverages and spices: Antioxidant activity and health effects—A review. Journal of Functional Foods. 2015;18:820-897.*

Gomes et al, Does medium chain triglyceride play an ergogenic role in endurance exercise performance, Revista Brasileira de Medicina do Esporte, 2003, vol. 9, No. 3, pp. 162-168.

Johanna Maria Hallebeek, Dietary control of equine plasma triglycerols, Thesis (University Utrecht), 2002, pp. 1-144+135-137.

O A Adefila et al, Characterisation of an alpha-amylase from sorghum (*Sorghum bicolor*) obtained under optimised conditions, Journal of the Institute of Brewing, 2012, vol. 118, No. 1, pp. 63-69.

J Martin et al, Chromium picolinate supplementation attenuates body weight gain and increases insulin sensitivity in subjects with type 2 diabetes, Diabetes Care, 2006, vol. 29, No. 8, pp. 1826-1832.

E Bertoft et al, Effect of pH, temperature, and calcium ions on barley malt alpha-amylase isoenzymes, Jounmal of the Institute of Brewing, 1984, vol. 90, pp. 298-302.

Stance Equine, PowerStance equine feed supplement, 2013, www.stanceequine.co.uk/product-powerstance and promotional video at www.youtube.com/watch?=vDAQSi8w5xU.

* cited by examiner

ENZYME-RICH MALT EXTRACT (ERME) FORMULATIONS

RELATED APPLICATIONS

This application is a national phase application filed under 35 USC § 371 of PCT Application No. PCT/GB2017/053516 with an International filing date of Nov. 23, 2017, which claims priority of GB Patent Application 1619789.9 filed Nov. 23, 2016. Each of these applications is herein incorporated by reference in its entirety for all purposes.

FIELD OF THE INVENTION

The present invention concerns novel formulations including enzyme-rich malt extract and kits comprising packaged formulations of the same. The present invention extends to feeds incorporating such a formulation and to the use of such formulations as veterinary or human medicaments.

BACKGROUND OF INVENTION

The applicant has previously determined that digestion in mammals might be improved by providing several different enzymes at once, to improve breakdown of plant-based products. Further, the bulk supply of such a product within a feedstuff is very useful commercially. It was additionally determined that enzyme-rich malt extract (ERME) may be medically useful in mammals, especially horses and particularly in relation to intestinal and/or metabolic disorders or disease, for example colic, acidosis or laminitis. It is also suggested by the applicants that treatment and/or dietary management of specific conditions inherently associated therewith is plausibly treatable by such ERME compositions due to the biological pathways that are known to give rise to such conditions. Such efforts in this area of research were first described in WO2013/136069.

In particular, the compositions as described above include a malt extract having a plurality of enzymatically active carbohydrases, including one or more amylases and optionally one or more fructanases. It is clear that animal feeds and supplements, in particular, horse feeds comprising such compositions would be useful in the capacity described above. As it concerns the particular use in equine mammals, such a composition is typically given with standard feed components such as vegetable material: grain or hay.

However, no other seemingly useful components were provided with ERME and those that were added, such as generic salts, linseed oil or electrolytes were believed to be of limited additional therapeutic benefit.

Further, traceability of a feed or product comprising the ERME composition is essential to be able to aid quality control in a commercial supply or distribution chain and provide some assurance to the end purchaser regarding authenticity, especially when it concerns a health risk to valuable animal assets, such as race horses.

Formulations providing specific further technical advantages are thought to be desirable; however it is also crucial to provide such formulations without reducing the enzyme activity of the ERME.

Very little work has been done in the equine field to further determine formulations of ERME that would be useful in this regard. The applicants have conducted investigation into possible formulations comprising ERME and it is from this work that the present invention arises.

SUMMARY OF INVENTION

The present invention concerns formulations comprising malt extract including a plurality of enzymatically active enzymes (ERME) including at least fructanase and amylase; one or more medium-chain triglycerides (MCTs) and/or at least one biologically acceptable marker.

In some embodiments the formulation may include a biologically acceptable marker or label, such as a metal marker, one or more MCTs or both of these components since both bring useful technical effects to the formulation of the invention comprising ERME.

In one embodiment the formulation comprises a chemical or biological marker integrated into the product, for example during the production of the ERME, which enables a user to determine if he or she has been provided with an authentic product, and thus from an authorised supplier or distribution channels originating from or in connection with the present applicant.

For example, the provision of a chemical marker, such as a metal, thereby provides means that the formulation of the invention maybe easily and cheaply tracked and identified by simple chemical testing. Such a marker will help assurance that a commercial product supplied is authentic and thus comprises the composition expected by the distributer, purchaser or end user.

In such an embodiment the one or more chemical metal marker may also provide therapeutic benefits enhancing use of that formulation in a human or other mammal, an animal such as a horse or a pony; further enhancing the ability to improve the condition and health and/or combating particular disease.

In particular, such a chemical marker may serve a dual purpose since, in addition to the tracking property; it is useful in optimising the activation of the enzymes in the formulation. Preferred markers include metals, such as chromium or calcium, which advantageously act as a therapeutic component and as a physical determiner of the product.

In some instances other metals such as magnesium or manganese may be appropriate. In particular calcium, such as a calcium salt, for example a sulphate ($SO_4$) can be used. Thus, in preferred embodiments the marker is a metal or metal salt, preferably wherein the metal is selected from chromium and/or calcium, manganese and/or magnesium, more preferably the metal salt is a sulphate or other equivalent functioning salt.

The formulation may comprise up to 0.5 w/w % of a biologically acceptable metal in the composition and most preferably approximately 0.1-0.2% w/w of the formulation. For example, in some embodiments the formulation may comprise a metal salt, such as calcium, although others with equivalent effect could be utilised.

In preferred embodiments the metal salt is provided as part of the malt extract (ERME) when formulated and thus the ERME itself may comprises 100 mg to 350 mg of a metal salt per L of mash product during production. In embodiments the ERME comprises 150 mg to 300 mg of metal salt per L of mash product during production and most preferably 200 mg/L. In preferred embodiments the metal salt is a calcium marker, such as a calcium salt. In some embodiments the metal salt is calcium sulphate.

Furthermore, such a formulation further provides the significant benefits as described above without a reduction of more than 50% in enzymatic activity of standardised ERME, which is the minimum acceptable activity.

The ERME may then be optimally formulated with other beneficial components such as MCTs. Selecting medium chain triglycerides (MCTs) for use with ERME in such a composition are useful for further improving the digestion of food whether in humans or equines; specifically the formulation optimises the digestive processing of the composition itself, as well as fundamentally increasing the glycogen availability in muscles.

Such formulations maybe particularly, although not exclusively, useful in horses, particularly race horses, where the digestive system is sensitive and digestive issues are improved by the action of ERME. However, the applicants assert that directly impacting short term energy efficiency and muscle performance via the additional action of a medium chain triglyceride will be still further useful. Improvements in the general condition of a premium animal, such as a race horse, over the medium to longer term may have considerable benefits and be of paramount importance, for example, effecting racing life duration and fertility.

It is envisaged that such formulations can therefore be helpfully used within animal feeds, most usefully in performance animal feeds such as horse feed or other feeds provided for highly valued animal assets. The present invention therefore extends to an animal feed or drinking solution comprising composition according to any preceding claim.

Such formulations are applicable for human consumption and further provide components that are particularly useful in treating disorders associated with enterometabolic malfunction such as IBS.

As it concerns compositions for use in mammals, this component will be equally beneficial to human pancreatic amylase, which is activated by fatty acids, the addition of MCT (which will hydrolyse to fatty acids) is therefore further boosts the activity of the enzymes in the gut.

Preferably the MCT is provided in a concentration of at least 10 mM. In some embodiments the formulation preferably comprises up to 10% MCT w/w, or more preferably up to 5% MCT w/w.

MCTs used in the formulation of the invention may include those having 2 or 3 different medium chain fatty acids (MCFAs) selected from: Caproic acid (6C); Caprylic acid (C8); Capric acid (C10); and Lauric acid (C12). The formulation preferably comprises up to 15% w/w MCT. MCTs containing a significant percentage of Lauric acid, such as 40-45% or more than 45% are preferred. In some embodiments the MCTs are provided by coconut oil.

The formulation may further comprise one or more therapeutically beneficial components selected from: Coenzyme Q, quercetin, lysine, threonine, glucosamine, N-acetyl cysteine and anti-oxidants such as pomegranate or blueberry extract.

Additionally, the formulation may also comprise one or more flavonoids, preferably a soy flavonoid.

The formulation may further comprise one or more excipients selected from bulking agents, stabilisers, thickeners, additional vitamins, minerals, edible oils, salts and/or electrolytes. It may be provided as a liquid or powder.

In one embodiment there is an animal feed comprising the formulation of the invention in combination with vegetable material. This may be a part of the animal's normal feed to increase the energy utilisation from the feed. The feed may be, for example, grains such as oats (including bruised, naked or rolled oats), barley or maize; hay such as Timothy hay, or alfalfa hay; or silage. A balancer, such as an oat balancer, may also be provided.

A kit comprising a packaged formulation of the invention as defined above and chemical test kit for identifying the one or more metal markers comprised therein.

The invention further extends to a formulation comprising: malt extract including a plurality of enzymatically active enzymes including at least fructanase and amylase; one or more medium-chain triglycerides and/or a biologically acceptable metal component, preferably selected from chromium and or calcium for use as a veterinary or human medicament.

In a preferred embodiment the invention concerns a formulation comprising: malt extract including a plurality of enzymatically active enzymes including at least fructanase and amylase; one or more medium-chain triglycerides and a biologically acceptable metal component, such as calcium, or a calcium salt, which has been shown to provide enhanced benefit to the composition.

The formulations of the invention are particularly suitable for use in the treatment and/or dietary management of an equine disorder, condition or disease and in particular where the condition is selected from equine insulin resistance, diabetes, laminitis and acidosis.

Furthermore, the applicant has good reason to believe the formulation will be equally applicable for use in the treatment and/or dietary management of a human condition mediated by enterometabolic gut disorders, which they have described in previous works, such as IBS or IBD. The present formulation is however the first disclosure of a formulation of ERME suited for this treatment purpose.

In some embodiments the invention concerns a kit comprising a packaged formulation of the invention with a tester or testing means for identifying the marker and/or metal. Such simple chemical tests are commercially available and known to the skilled person.

DESCRIPTION

The following components of the formulations of the invention are described in further detail:

ERME

Malted grains allow the production of malt extract including a plurality of enzymatically active enzymes, i.e. enzyme-rich malt extract (ERME) as used in the present invention. The enzymes must have enzyme activity or a substrate, for example treating starch down into one or more smaller components such as mono- or di-saccharides. The extract comprises a plurality of enzymes including carbohydrases, capable of breaking down one or more carbohydrates into smaller components, or proteases. Typically the enzymes are one or more amylases and/or one or more fructanases. Amylases catalyse the breakdown of starch into sugars.

a-Amylase breaks starch down. It yields maltotriose and maltose from amylose, or maltose, glucose and limit dextrin from amylopectin.

β-Amylase breaks starch into maltose. Both a-amylase and β-amylase are found in seeds during germination. Both a- and β-amylase may be present.

Fructanases break down fructans, which are believed to be involved in the induction of laminitis in hoofed animals. Fructanases include2, I-P-D-fructan hydrolases.

Production processes for deriving malt extract are known in the art and have been described by the present applicants previously. For example, the malt used is typically green or has high diastatic power (high dp) malt; the germinated seeds have been heated and dried above 40° C., 50° C. or 55° C. but below 75° C. or 70° C. to halt germination—as this often reduces the activity of enzymes remaining after that heating step. Typically water is added and heated to at least approximately 40° C. or 50° C. to form the mash. The temperature may be raised to 55° C., 60° C. or 65° C. but below 75° C. or 70° C. and then separated from the grain. The liquid wort may be evaporated by, for example, vacuum evaporation.

A malt extract may be prepared by, for example, crushing the malt and extracting the enzymes with, for example, hot water. The extract may then be evaporated, for example to an 80% sugar solution containing the enzymes (an "enzyme rich extract").

Diastatic power is measured in ° Lintner (° L) or by Windisch Kolbach Units (° WK). A malt with enough power to self-convert into starch has a diastatic power near 35° Lintner. A high diastatic malt typically has a value of above 35° Lintner (94° WK), or typically above 45° L, 50° L, 60° L, 70° L or above 80° L.

A variety of seeds may be used to produce the malt. For example, wheat, triticale, sorghum, maize, buck wheat or rice may be used. Barley is typically used and most preferred as this is regularly used as a source of malt for the brewing industry, in readily available and malt flavour is generally well accepted by mammals. The most preferred embodiment concerns a spray dried diastatic malt extract from barley wherein the process requires hot water extraction of high diastatic malted barley, followed by filtration, vacuum evaporation and spray drying. The malt extract is a cream coloured, fine powder that is sweet with a malty flavour. The powder has a moisture content of 6% and a Diastatic power of 50° L or more.

The formulations of the invention may comprise up to 95 w/w % ERME.

Medium Chain Triglycerides (MCT)

The triglycerides selected for use in the formulation of the invention are specifically medium-chain triglycerides (MCTs) composed of a glycerol backbone and 2 or 3 medium-chain fatty acids (MCFAs) with 6-12 carbon atom aliphatic tail selected from Caproic acid (6C) Caprylic acid (C8), Capric acid (C10) and Lauric acid (C12).

Well known sources of MCT include palm kernel oil and coconut oil. Coconut oil is particularly preferred having approximately 45% Lauric acid, which may be digested in the biliary micelle and absorbed into the intestinal lacteal. Most preferably the MCT has a maximum of 5% 6C MCFA, 55-65% 8C MCFA, 35-45% C10 MCFA and up to 2% C12 or C14 MCFAs.

MCTs have the advantage of being easily absorbed into the equine bloodstream and so being more quickly and readily available. MCTs are particularly useful since they metabolise and are rapidly absorbed without loss in energy efficiency; they are known to passively diffuse from the gastrointestinal tract to the portal system without requirement for breakdown, as compared to longer chain fatty acids and not require other digestion aids. Further they do not block the absorption of other key nutrients. This source of fat is incredibly important for horses and can be used as an energy source for performance, thus preserving muscle glycogen and promoting stamina.

The composition or formulation of the invention may have up to 10% w/w MCT.

Furthermore, the end product, having a proportion of MCT, inherently comprises lower solids in its final formulation this form may be extracted or slide from the packaging, such a sachet or the like, with greater ease.

Marker/Label

The provision of a marker and particularly a metal marker is particularly advantageous in the ERME formulation because it is often both biologically and physically useful. This is therefore a particularly preferred embodiment of the invention.

Therapeutic Properties

Most preferred markers are metals that provide a therapeutic enhancement with the ERME, for example Chromium, which has been shown to reduce insulin resistance and promotes glucose tolerance (J ANIM SCI 1995, 73:1123-1130. Amoikon et al.). Such a metal is particularly useful when provided with ERME to combat horses or ponies with insulin resistance and which may be prone to laminitis. In particular, Tri-valent Chromium compounds, for example, chromium tri-picolinolate appear to have little toxicity and thus can be used safely in such formulations (Martin J et al, Diabetes Care 2006 August; 29 (8): 1826-1832. http://dx.doi.org/10.2337/dc06-0254).

Calcium, for example, in the form of calcium sulphate, may be used as a marker with both therapeutic and physical tracking properties. The enzyme amylase enzyme contains at least one calcium-binding site and calcium is therefore useful in optimising the activation of such an enzyme.

For example, 0.1% calcium chloride achieves an achieve enhanced activation of the enzyme but $Ca^{2+}$ ions will be surfeit in the composition permitting tracking via a composition testing process if required. Such an addition therefore provides dual purpose in the resulting formulation. The calcium maybe added during the mashing stage when the enriched enzyme is produced from malt.

Other Components

Certain flavonoids, such as soy flavonoids, for example, genistein and daidzein, may also provide functionality to the therapeutic nature of the composition. Flavonoids activate the enzyme tyrosylprotein sulfotransferase (TPST) which is essential for forming mucins, the proteins which line the mammal gut wall.

The enzyme exists as 2 isoforms, TPST-1 and TPST-2 which are activated by 20 mM manganese (Mn) chloride while TPST-2 is activated by 15 mM magnesium (Mg) chloride as well. In particular such components may be beneficial in a composition suitable for any mammal in which ERME provides a positive effect such as medical use in equines or humans.

Where flavonoids are provided in the composition of the invention, in some embodiments metals such as Mg or Mn may be added instead, or in addition to, the existing tracking metal.

Marker Properties

The marker may be in the form of a metal; however, the applicant envisages that other components, whether biological or chemical in nature might be useful alternatives because whether a metal or not, this component acts as a means to trace the formulation and final product.

In one embodiment, simple chemical testing can be provided in a kit to verify if the formulation comprises said marker or particular metal, enabling cheaper or non-authentic products to be identified and disposed of efficiently before they are used as feed to horses.

A means of identifying whether a product is potentially counterfeit and hence substandard in a supply chain is very commercially valuable. Default verification, i.e. determining that a particular batch is not authentic is important because the provision of any nutrition, such as a food or supplement, to such an animal always presents a source of risk to health which should be minimised. Race horses require considerable investment to purchase and maintain and thus represent an asset which is highly protected by the owner.

It is therefore useful to be able to demonstrate to purchasers that the risk taken by the owners, purchasers, sellers and trainers in providing such a feed to their performance horses is minimised; routine testing able to be carried out by distributors/purchasers would, in most cases, establish if a different product, where the quality may not be guaranteed, had been obtained.

EXAMPLE FORMULATIONS

Example 1

ERME up to 90-99.9%

In the preferred formulations of Example 1 up to 0.5% of a metal marker or up to 10% of MCT can be used in combination with the ERME. The metal may however be formulated as part of the ERME production process.

Example 1b

ERME 90-95%
Metal 0.1%-0.5%
MCT 4.5-9.9%

Example 2

ERME 95%
2a Metal 0.5% MCT 4.5%
2b Metal 0.4% MCT 4.6%
2c Metal 0.3% MCT 4.7%
2d Metal 0.2% MCT 4.8%
2e Metal 0.1% MCT 4.9%

Example 3

ERME 90%
4a Metal 0.5% MCT 9.5%
4b Metal 0.4% MCT 9.6%
4c Metal 0.3% MCT 9.7%
4d Metal 0.2% MCT 9.8%
4e Metal 0.1% MCT 9.9%

The most preferred metals are calcium and chromium, wherein up to 0.5 w/w of the composition comprises calcium or wherein up to 0.5 w/w of the composition comprises chromium. As described previously, in some embodiments manganese or magnesium maybe particularly preferable.

Other Components

The formulation of the invention may additionally benefit from one or more of the following components; Co-Enzyme Q, Quercetin, lysine, threonine, glucosamine, N-acetylcysteine, anti-oxidants such as pomegranate, blueberry extracts, in which case the composition of the formulated examples above may be modified accordingly.

Quercetin is thought to both promote formation of ATP and give more energy and thus may enhance the performance capability in a horse.

Lysine and/or threonine are essential amino acids in horses and may be preferable in a formulation concerned with amino acid metabolism and protein synthesis. Glucosamine is particularly concerned with reducing breakdown of cartilage and promote its regrowth. N-acetyl cysteine promotes formation of glutathione, involved in crucial enzyme processes, in the liver.

Certain fruit oils or extract from pomegranate and blueberry contain antioxidants and hence are thought to be valuable in such formulations.

Certain components are explicitly not included in the present invention formulations, such as yeast or other means by which the maltose will be fermented.

In-Vitro Enzyme Activity Testing

A minimum enzyme activity of the ERME-based formulations of the invention is retained despite the additional components provided therein. To this end the applicant such formulations, as provided at least in the examples herein retain the desired or at least minimum level of enzymatic activity for the proposed use by undertaking a comparative diastatic assay even when combined to form novel formulations of the proposed inventions and embodiments thereof It is understood that the addition of the metal to the extracted enzymes in a post formulation step, e.g. in the form of calcium sulphate provides an easy and inexpensive production process, rather than for example using water enriched with calcium during the extraction process.

The results on the addition of Ca, for example on the form of Calcium sulphate, on enzyme activity are as follows:

Diastatic Trial: to assess the effect of adding Calcium Sulphate to a mash of HDP malt has on the DP (diastatic potential) of the liquid extracted from the mashing process during the production of malt.

Method: using batch number D5572 HDP malt and mashing at 2.5:1 with the following mash profile process:

Mash @ 48° C.
Hold @ 48° C. for 60 mins
Raise to 63° C.
Hold @ 63° C. for 15 mins
Run Off
Sample product after 1 L run off
Mash 1: Control with no additions
Mash 2: add 200 mg/l of calcium Sulphate
Mash 3: Add 400 mg/I of calcium Sulphate.
Results: corrected to 80% brix

|  | Standard Mash | Mash 2 | Mash 3 |
| --- | --- | --- | --- |
| Wort Solids | 15.3 | 13.4 | 13.1 |
| pH |  | 6.09 | 6.15 |
| DP | 121 | 186 | 145 |
| DU | 82 | 92 | 88 |

The addition of calcium to the mash enhances the enzyme activity seen here as a clear rise in diastatic potential. The increase in calcium beyond a set addition does not appear to aid any further development and may in fact decrease activity indicating there is an optimum range for the addition of such metal activity enhancers. The invention is therefore relevant particularly to this preferred range In-Vivo and Ex Vivo Technical Formulation The examples and embodiments of the invention demonstrate a useful technical solution to counterfeiting issues, including a practical traceable effect and therapeutically beneficial effect for use in equine veterinary distribution channels particularly.

Marker Testing and Product Identification

The presence of a surplus of metal ions, such as calcium, is sufficient to provide a single field test, such as a flame test, to confirm the presence of calcium in the formulation. However, thereafter the formulation retains sufficient calcium to provide an additional therapeutic function in combination with the active enzyme components of the invention.

The invention claimed is:
1. A formulation comprising:
  enzyme rich malt extract including a plurality of enzymatically active enzymes including at least fructanase and amylase; and
  at least one biologically acceptable marker, wherein the at least one biologically acceptable marker is calcium, wherein the biologically acceptable marker has a concentration of 0.1-0.5% w/w formulation, wherein the enzyme rich malt extract is derived from barley seeds, wherein the amylase comprises alpha amylase and beta amylase, and wherein the formulation is processed and configured to be stored at a temperature equal to or less than 75 degrees Centigrade.

2. The formulation of claim 1, wherein the formulation comprises up to 10% Medium Chain Triglycerides (MCTs) w/w.

3. The formulation of claim 1, wherein the formulation comprises 2 or 3 different medium chain fatty acids (MCTs) selected from the group consisting of: Caproic acid (6C); Caprylic acid (C8); Capric acid (C10); and Lauric acid (C12).

4. The formulation of claim 1, further comprising a Medium Chain Triglyceride (MCT) comprising 40% w/w or more Lauric acid.

5. The formulation of claim 1, further comprising a Medium Chain Triglyceride (MCT) provided by coconut oil.

6. The formulation of claim 1, wherein the formulation further comprises one or more therapeutically beneficial components selected from the group consisting of: Coenzyme Q, quercetin, lysine, threonine, glucosamine, N-acetyl cysteine, and an anti-oxidant.

7. The formulation of claim 1, wherein the formulation further comprises one or more excipients selected from the group consisting of: bulking agents, stabilisers, thickeners, additional vitamins, minerals, edible oils, salts, and electrolytes.

8. The formulation of claim 1, wherein the formulation further comprises one or more flavonoids.

9. The formulation of claim 1 wherein the formulation is configured for use as a veterinary medicament.

10. The formulation of claim 1 wherein the formulation is configured for use in the treatment and/or dietary management of an equine disorder, condition, or disease.

11. The formulation according to claim 10, wherein the condition is selected from the group consisting of equine insulin resistance, diabetes, laminitis, and acidosis.

12. An animal feed comprising the composition of claim 1, further comprising one or more of vegetable material selected from the group consisting of one or more of oats, barley, maize; hay; silage; and an oat balancer.

13. The formulation of claim 1, wherein the formulation comprises up to 5% MCT w/w.

14. The formulation of claim 1 wherein the at least one biologically acceptable marker is a sulphate or other equivalent functioning salt.

15. The formulation of claim 8 wherein the flavonoid is a soy flavonoid.

16. The formulation of claim 6 wherein the anti-oxidant is a pomegranate or blueberry extract.

* * * * *